United States Patent [19]

Mathewson

[11] Patent Number: 5,263,924
[45] Date of Patent: Nov. 23, 1993

[54] INTEGRATED LOW PRIMING VOLUME CENTRIFUGAL PUMP AND MEMBRANE OXYGENATOR

[75] Inventor: Wilfred F. Mathewson, Bonsall, Calif.

[73] Assignee: Baxter International Inc., Deerfield, Ill.

[21] Appl. No.: 765,307

[22] Filed: Sep. 25, 1991

[51] Int. Cl.⁵ .............................................. A61M 1/03
[52] U.S. Cl. ........................................ 604/4; 422/44; 422/45
[58] Field of Search ...................... 261/28; 422/44, 45, 422/48; 210/321.63, 321.76, 321.78; 604/4, 5, 6

[56] References Cited

U.S. PATENT DOCUMENTS

| | | | |
|---|---|---|---|
| 2,876,769 | 3/1959 | Cordova | 128/214 |
| 3,139,832 | 7/1964 | Saunders | 103/103 |
| 3,183,908 | 5/1965 | Collins et al. | 128/214 |
| 3,487,784 | 1/1970 | Rafferty et al. | 103/103 |
| 3,674,440 | 7/1972 | Kitrilakis | 23/258.5 |
| 3,771,658 | 11/1973 | Brumfield | 210/186 |
| 3,771,899 | 11/1973 | Brumfield | 415/90 |
| 3,841,837 | 10/1974 | Kitrilakis et al. | 23/258.5 |
| 3,893,920 | 7/1975 | Hubbard et al. | 210/197 |
| 3,901,623 | 8/1975 | Grennan | 415/141 |
| 3,977,976 | 8/1976 | Spaan et al. | 210/321 |
| 3,989,626 | 11/1976 | Bentley et al. | 210/177 |
| 4,253,798 | 3/1981 | Sugiura | 415/213 |
| 4,312,757 | 1/1982 | Brumfield | 210/646 |
| 4,346,006 | 8/1982 | Kopp et al. | 422/48 X |
| 4,400,275 | 8/1983 | Ramshaw et al. | 210/321.1 |
| 4,713,176 | 12/1987 | Schoendorfer et al. | 210/645 |
| 4,715,953 | 12/1987 | Leonard | 210/321.8 |
| 4,755,300 | 7/1988 | Fischel et al. | 210/650 |
| 4,790,942 | 12/1988 | Shmidt et al. | 210/650 |
| 4,808,307 | 2/1989 | Fischel et al. | 210/321.68 |
| 4,808,328 | 2/1989 | Nakanishi et al. | 261/DIG. 28 X |
| 4,876,013 | 10/1989 | Shmidt et al. | 210/650 |
| 5,017,103 | 5/1991 | Dahl | 417/420 |
| 5,120,501 | 6/1992 | Mathewson et al. | 261/DIG. 28 X |
| 5,139,741 | 8/1992 | Hagiwara | 261/DIG. 28 X |

FOREIGN PATENT DOCUMENTS

| | | |
|---|---|---|
| 0089122 | 2/1983 | European Pat. Off. |
| 2301084 | 7/1973 | Fed. Rep. of Germany ........ 422/45 |
| 3923692A1 | 1/1991 | Fed. Rep. of Germany. |
| WO90/04419 | 10/1989 | PCT Int'l Appl. |

OTHER PUBLICATIONS

"The Taylor-Vortex membrane oxygenator: design analysis based on a predictive correlation for oxygen transfer", J. D. S. Gaylor and L. C. Smeby, *Physiological and Clinical Aspects of Oxygenator Design*, Elsevier North-Holland Biomedical Press, 1976.

*Primary Examiner*—Robert A. Hafer
*Assistant Examiner*—Sam Rimell
*Attorney, Agent, or Firm*—Karen Lee Orzechowski; Bruce M. Canter

[57] ABSTRACT

A low priming volume integrated centrifugal pump and membrane oxygenator comprising a housing containing a mass transfer bed comprising gas permeable hollow membrane fibers placed circumferentially in a ring around an impeller. The mass transfer bed is formed by a multiple wrap of a fiber ribbon comprising at least two layers of fibers bonded in precise orientation with fibers in alternate layers are positioned in line with the opening between fibers in the layers above and below. Adhesion means ensure precise orientation of the fibers. Priming volume is further reduced by a small impeller flow channel volume.

35 Claims, 4 Drawing Sheets

INTEGRATED LOW PRIMING VOLUME CENTRIFUGAL PUMP AND MEMBRANE OXYGENATOR

FIELD OF THE INVENTION

The invention relates to extra corporeal device technology for the support of patients during open heart surgery and in emergency situations requiring extracorporeal cardiopulmonary support. In particular, the invention relates to new and useful improvements in apparatus for the pumping and oxygenation of blood to temporarily replace the cardiac and pulmonary functions of a patient.

BACKGROUND OF THE INVENTION

During open heart surgery and in some emergency cardiopulmonary situations, it is necessary to have some means for pumping the blood and some means for oxygenating the blood to replace or support the patient's cardiopulmonary functions. Mechanical substitutes for doing this can operate by taking blood from the patient's venous system and oxygenating it by dispersing it over one face of a membrane area and exposing the opposite face to an atmosphere of pure or nearly pure oxygen. After the blood absorbs oxygen in this environment, it is forced by means of a pump into the arterial system of the patient.

Prior art extracorporeal device technology has used individual devices for the functions of pumping blood and oxygenating blood. For example, a pump would be used in conjunction with an oxygenator. Typically, these devices are connected together in an extracorporeal tubing loop to receive venous blood from the patient and return arterial blood back to the patient. One of the problems with these types of devices, such as that shown in U.S. Pat. No. 3,183,908, has been that large amounts of blood are required to prime the oxygenator, the pump, and the tubing between the oxygenator and the pump.

Some attempts have been made to incorporate the pumping and oxygenation functions in a single device. For example, U.S. Pat. No. 3,841,837 discloses a blood oxygenator or dialyzer that achieves enhanced transfer through rotation of a cylindrically mounted membrane placed eccentrically inside a stator housing. Blood flows in the annular space between the rotor and the stator. Rotation causes a pumping action, thus causing pumping and oxygenation to occur simultaneously. All of these prior art devices have required relatively large amounts of fluid to prime the pump and oxygenator. There have also been difficulties with the safety and ease of use by the perfusionist. Furthermore, these devices can be quite costly to manufacture.

SUMMARY OF THE INVENTION

The present invention is directed to a low priming volume integrated centrifugal pump and membrane oxygenator through which the blood is pumped then oxygenated. The integrated pump and oxygenator comprises a housing containing a mass transfer bed for oxygenating and an impeller for pumping. The fluid entering the housing is directed by the impeller through the mass transfer bed, which is in the form of a fiber membrane ring surrounding the impeller. A gap is located between the impeller and ring to insure safe rotation of the impeller. The size or extent of the gap will depend upon the amount of secondary flow desired to enhance oxygenation between the blood in the gap and the first fiber membrane layer or layers, while considering the added prime volume that occurs with increasing gap size.

The surface area requirements for mass transfer place some design conditions on the height and diameter of the fiber membrane ring, which in turn, influences the design of the matching impeller. This could produce an unacceptably high prime volume if the impeller were designed in the conventional manner with relatively thin vanes. This problem is overcome by use of an impeller with small volume flow channels in comparison with the total envelope volume of the impeller. The small impeller flow channel volume requires a greatly reduced priming volume and has the effect of reducing the amount of pump turbulence.

The mass transfer bed comprises a ring of gas permeable hollow fibers running circumferentially around the impeller. This ring can be formed in any manner. A preferred embodiment is to create the fiber ring by using a multiple wrap of a preformed fiber ribbon. This fiber ribbon can be constructed from at least two layers of fibers bonded together in precise orientation in an arrangement where the fibers in alternate layers are positioned in line with the opening between fibers in the layers above or below. In a further embodiment, adhesive means can be used to achieve the precise orientation of the fibers in the ring.

Figure 1:
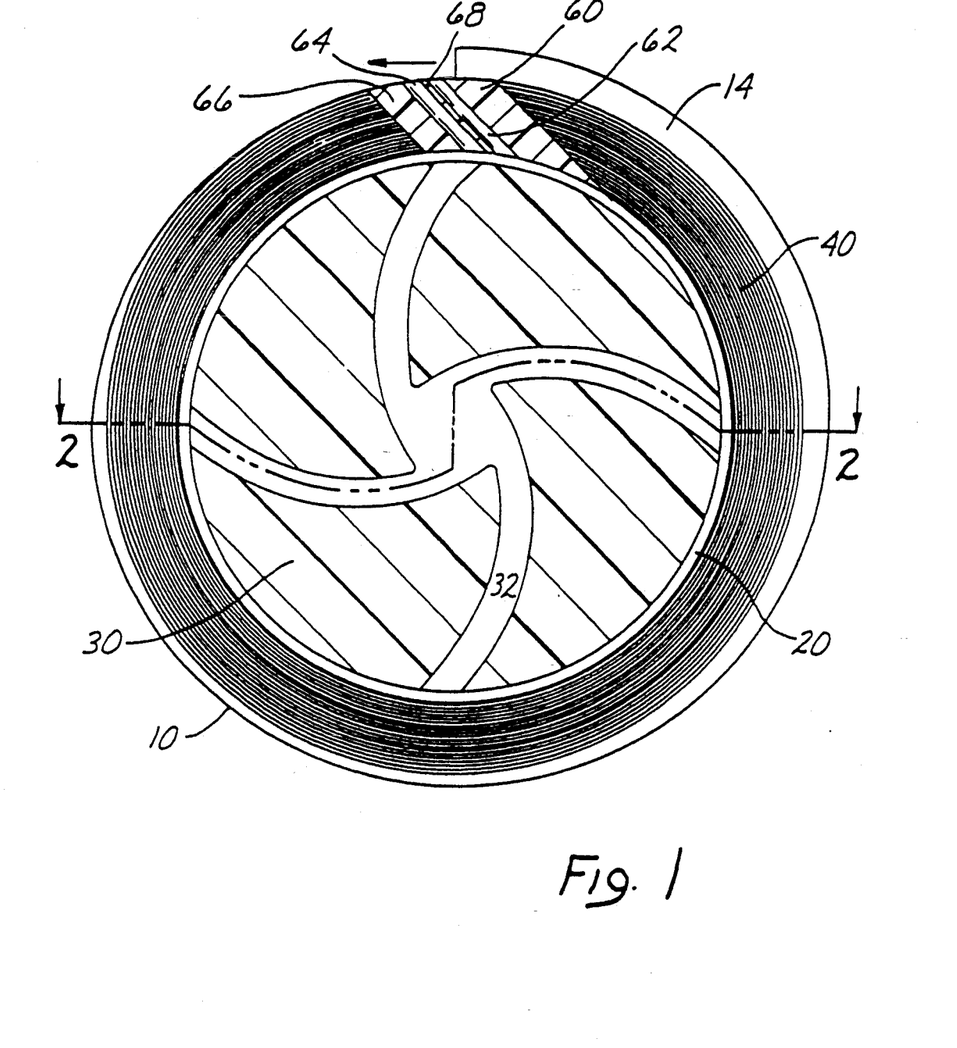
FIG. 1 is a schematic top plan view of the integrated centrifugal pump and membrane oxygenator of the present invention.
Figure 2:
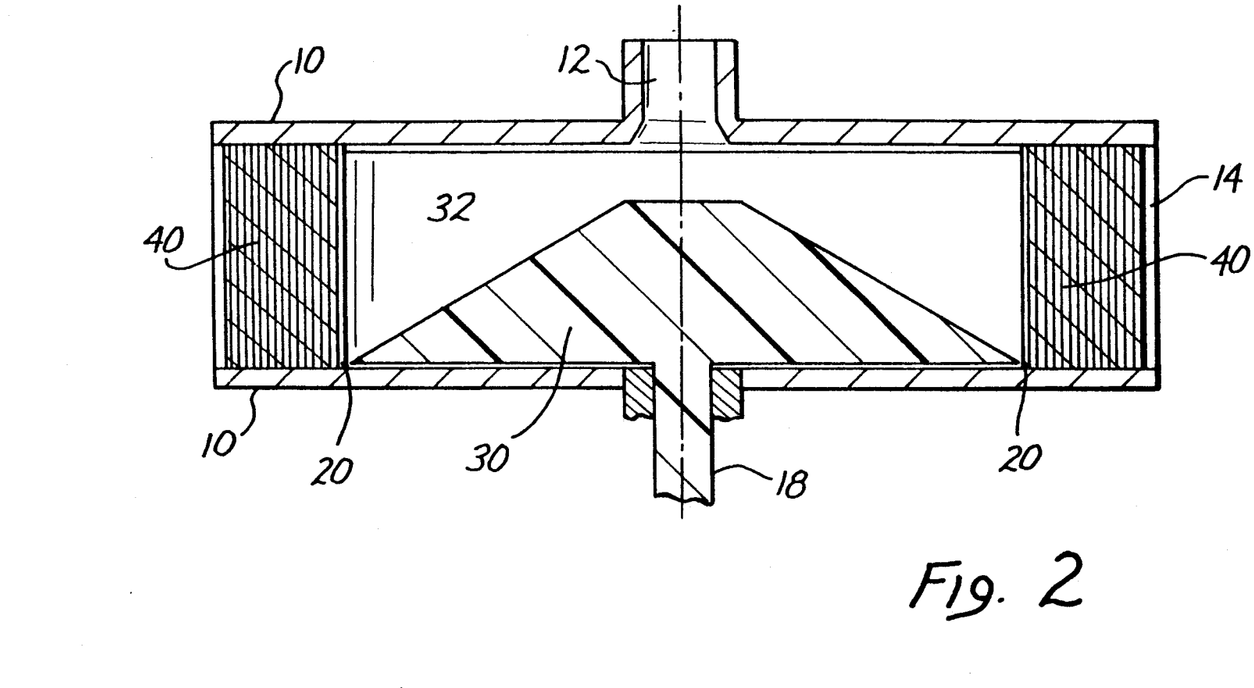
FIG. 2 is a sectional view taken on line 2—2 of FIG. 1.

DETAILED DESCRIPTION OF THE INVENTION to FIGS. 1 and 2, the low priming volume integrated centrifugal pump and membrane oxygenator of the present invention comprises housing 10 containing impeller 30 surrounded by mass transfer bed 40. The top and bottom of the mass transfer bed 40 are sealed to the upper and lower internal faces of housing 10. Fluid entering housing 10 through fluid inlet 12 is pumped by impeller 30 through mass transfer bed 40. In mass transfer bed 40 the fluid is oxygenated and the carbon dioxide is removed. The fluid is then collected and discharged through a tapered exit manifold 14 located around the outer diameter of mass transfer bed 40.

The low priming volume of the integrated centrifugal pump and oxygenator of the present invention is a result of more than the mere housing integration of a pump and an oxygenator resulting from the reduction in the required manifolding and amount of tubing and connector priming volume. Priming volume is also reduced by other features cf the present invention described below.

As shown in FIG. 1, impeller 30 has flow channels 32 that act to force the fluid through the mass transfer bed 40. As impeller 30 rotates, flow channels 32 deliver uniform radial flow to the mass transfer bed 40 in the course of its 360 degree rotation. This uniform radial flow enhances oxygenation by insuring that the mass transfer bed 40 is uniformly perfused with blood to be oxygenated. The rotation of the impeller 30 insures true and uniform radial flow over the entire circumference and height of the mass transfer bed 40. As the flow channel 32 passes a segment of the mass transfer bed 40, a local flow pulse is created followed by a quiescent period until the next flow channel 32 arrives. This pulse enhances mass transfer, in particular, oxygenation and carbon dioxide removal. Additionally, the rotation of impeller 30 causes fluid mixing to occur in the gap 20 between the outer diameter of the impeller 30 and the inner diameter of mass transfer bed 40. This fluid mixing has the effect of further enhancing mass transfer of the blood in the gap 20 and the first few layers of fibers 38 in mass transfer bed 40.

The flow channel volume of flow channels 32 is relatively small compared with the envelope of the impeller 30. This is direct contrast to conventional radial impellers for centrifugal pumps. Conventional centrifugal pumps generally operate in a region of higher flow rates for a given required delivery pressure. Typical impellers have thin vanes with wide flow channels between the vanes to keep the flow channel volume as close to the maximum volume available as possible to create high flow rates. However, in extracorporeal cardiopulmonary support, relatively low flow and high pressure is required. Thus the impeller diameter and RPM requirements are dictated more by delivery pressure than flow demands. The small flow channel volume of the present invention results in high fluid delivery pressures at adequate flow rates, and thus allows the priming volume to be reduced. Another effect of the small flow channel volume is reduced turbulence in the pumping portion of the integrated pump and oxygenator.

The volume of flow channels 32 should be of a size to permit relatively laminar flow of the fluid in the impeller 30 so as to control friction losses and to minimize blood damage. Preferably the flow channel volume is from about 5% to about 60% of the total envelope volume. More preferably the flow channel volume is less than 50% of the total envelope volume. Most preferably the flow channel volume is from about 5% to about 30% of the total envelope volume. The flow channel volume can be altered by any means such as adjusting the size, shape and number of the flow channels.

Impeller 30 should be of a size sufficient to force the fluid through the mass transfer bed 40 and to return it to the patient without the need for an external pump. Preferably, the impeller 30 has a diameter of from about 2 inches to about 6 inches. The pump, including impeller and housing, can be made from any inert material that will not react with the blood or the oxygen. For example, the pump, impeller and housing may be molded from plastic materials such as polycarbonate and the like.

The mass transfer bed 40 of the integrated pump membrane oxygenator is where the oxygenation of the fluid takes place. The mass transfer bed 40 is preferably in the form of a ring of gas permeable, hollow fibers where the fibers run circumferentially around the ring. The mass transfer bed 40 can be constructed by any suitable means. The simplest construction is a plain winding of fiber. Alternatively, a fiber mat, such as the commercially available Enka TM fiber mat, could be used. Preferably, the mass transfer bed 40 is formed from a multiple wrap of a preformed fiber ribbon 42 such as that depicted in FIGS. 3 and 4. The fibers in the mass transfer bed 40 are held in position relative to one another by any suitable means such as adhesive points or filaments. The mass transfer bed 40 has a gas inlet header 60 and gas inlet manifold 62 to allow the passage of a second fluid, the oxygen gas, into the lumens 46 of the fibers 38. The second fluid exits the lumens 46 by means of gas outlet manifold 64 and gas outlet header 66, while maintaining separation of the second fluid from the first fluid. Manifold partition 68 separated the gas inlet header 60 and gas inlet manifold 62 from gas outlet header 66 and gas outlet manifold 64.

The gas inlet and outlet headers 60 and 66 may be formed by any conventional means. In a preferred embodiment, the gas inlet and outlet headers are created by potting a region with a urethane, a modified UV curable urethane, epoxy, or hot melt adhesive. The center portion of the potted region is then removed to expose the lumens and allow passage of a second fluid through them. A manifold partition 68 is placed in the open center portion to separate the gas inlet header 60 and gas inlet manifold 62 from the gas outlet header 66 and the gas outlet manifold 64. The gas inlet manifold 62 and the gas outlet manifold 64 communicate with appropriate inlet and outlet connectors in the housing 10. The header boundaries are selected for optimal flow and may range between tangential and radial.

The mass transfer bed 40 operates to oxygenate the first fluid, the patient's blood, by means of the lumen 46 of each fiber 38. The lumens 46 deliver the second fluid, the oxygenating gas, to the membrane wall 44 of the fiber 38. This membrane wall 44 is permeable to gas but not liquid. When liquid flows around the exterior of the fibers 38, the gas in the lumens 46 diffuse through membrane wall 44 into the liquid, thus resulting in oxygenation of the liquid. At the same time, carbon dioxide may be removed from the liquid by allowing the carbon dioxide in the liquid to diffuse through membrane wall 44 into lumens 46 where it exits the housing 10 by means of gas outlet manifold 64 with any unused oxygenating gas. The membrane wall 44 may be formed from any suitable material that permits the diffusion of oxygen and carbon dioxide while preventing the diffusion of the liquid. Some suitable materials include microporous polypropylene, polyethylene, silicone rubber and its derivatives.

The mass transfer bed 40 is of a sufficient size to permit it to be sealed to the upper and lower internal faces of housing 10. Preferably, the mass transfer bed 40 has a radial thickness ranging from about 1/10 inch to about 1 inch. The mass transfer bed 40 may be bonded to the housing 10 using conventional materials such as polyurethane, epoxy and the like.

Figure 3:
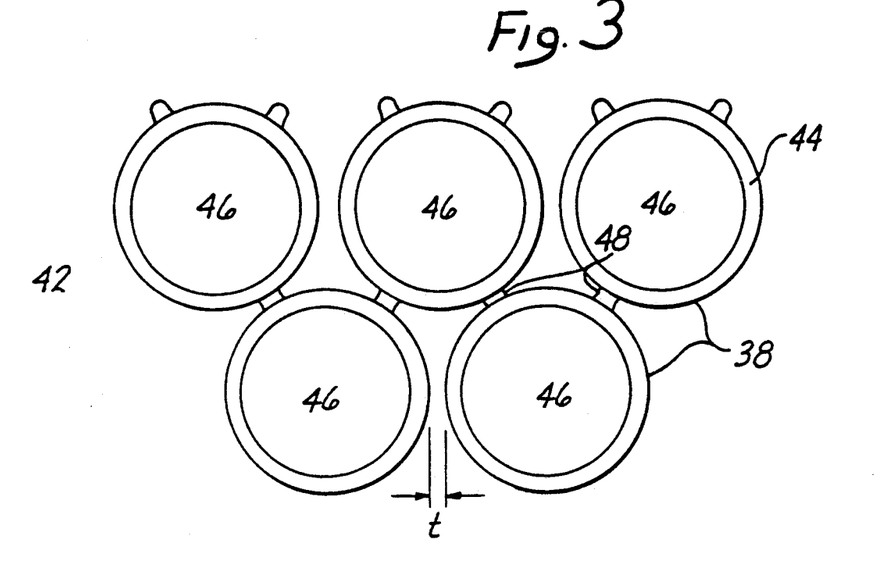
FIG. 3 is an enlarged sectional view of a portion of one embodiment of the fiber tape used to make the mass transfer bed shown in FIG. 1.
Figure 4:
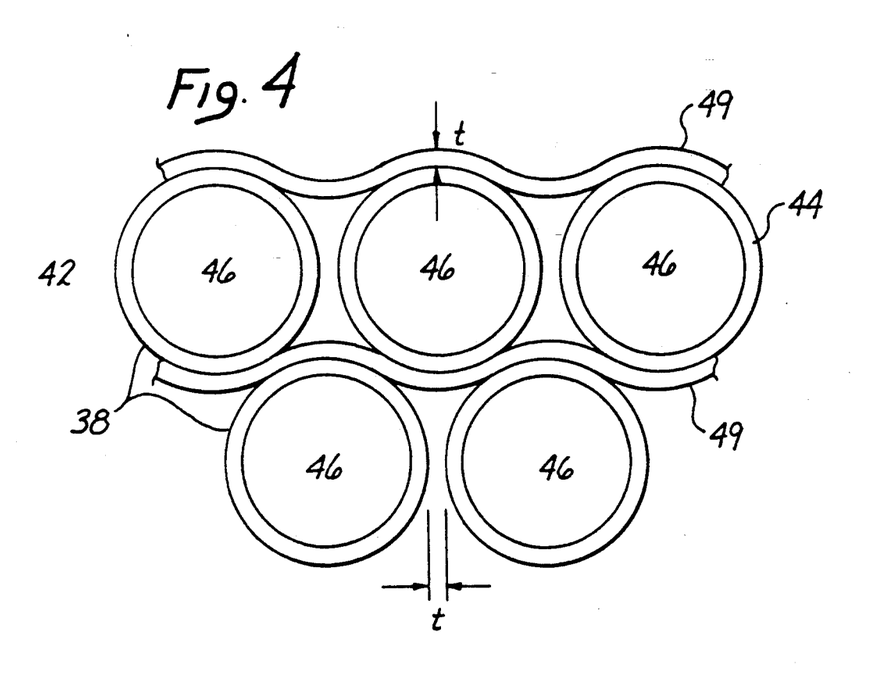
FIG. 4 is an enlarged sectional view of a portion of another embodiment of the fiber tape used to make the mass transfer bed shown in FIG. 1.

Fiber ribbon 42 that makes up mass transfer bed 40 is formed from at least two layers of fibers 38 bonded together to form a ribbon of the appropriate height. The fibers 38 are spaced in an alternating arrangement as depicted in FIGS. 3 and 4 so that the fibers in alternate layers are positioned in line with the opening between fibers in the layers above or below. FIGS. 3 and 4 show only a portion of the fiber ribbon 42. This arrangement results good mixing of the blood between the layers. This precise orientation of the fibers 38 in the fiber ribbon 42 is achieved by fixing the fiber position with an adhesion means. The adhesion means may be in the form of point attachments 48 as depicted in FIG. 3 or in the form of adhesive filament 49 as shown in FIG. 4. Preferably the lengthwise spacing pattern of these attachments 48 or filaments 49 is from about 0.050 inch to about 0.125 inch. Any conventional adhesive may be used such as an epoxy or a urethane or modified urethane cured by heat, catalyst or ultraviolet radiation. A hot melt adhesive may also be used. The use of such a precision orientation means allows optimum orientation of the fiber layers that simply cannot be achieved by use of single layer wraps.

For the simplicity of illustration, the fiber ribbon 42 is depicted schematically as a double layer ribbon in FIGS. 3 and 4. The fiber ribbon 42 may consist of multiple layers. At least two layers should be used to ensure precise orientation of the fibers 38 relative to each other. Preferably, the fibers 38 used to construct fiber ribbon 42 have an outside diameter of from about 200 microns to about 600 microns and an inside diameter of from about 150 microns to about 500 microns. More preferably, the fibers 38 would have a uniform spacing, t, between the fibers of from about 25 microns to about 100 microns.

The fiber ribbon 42, because of the uniformly thin spacing between fibers, requires a significantly smaller priming volume than other known fiber membrane oxygenators. The thin uniform spacing t between the fibers 38 also results in highly efficient oxygenation, thus requiring less membrane surface area and thus less prime volume.

The fiber ribbon 42 is would into a ring of appropriate thickness to fit into the housing 10 while allowing free rotation of impeller 30. Preferably, the height of the fiber ring 40 is about the height of the impeller 30. Most preferably, the impeller 30 and fiber ring 40 have a height ranging from about ¼ inch to about 2 inches.

As shown in FIGS. 1 and 2, there is a gap 20 located between the outer edge of the impeller 30 and the innermost portion of fiber ring 42. The gap 20 is an open area that during operation is filled with the fluid to be oxygenated. Proper selection and control of gap 20 can result in enhancing oxygenation in the innermost layer or layers of the fiber ring 42. This is due to a secondary or eddy flow created in gap 20 by the tangential flow component created by impeller flow channel 32. Care must be taken to select a gap 20 of sufficient size to enhance oxygenation while making sure that gap 20 is not so large as to increase the priming volume required. Preferably gap 20 will be from about 0.010 inch to about 0.100 inch.

Preferably the gap 20 is a size that permits the creation of Taylor vortices in this region. Taylor vortices are a known hydrodynamic phenomena that appear in a viscous fluid when it is placed between an outer stationary cylinder and an inner rotating cylinder. As discussed by Schlichting in *Boundary-Layer Theory* 7th Ed., McGraw-Hill, 1979, instabilities in fluid flow between concentric cylinders where only the inner cylinder is in motion were first investigated by Lord Rayleigh, who performed calculations based on the assumption that the fluid was non-viscous. Taylor, using a framework of linear theory and considering viscous fluids, found that when a certain Taylor's number was exceeded, axially circumferential vortices appear, which rotate in alternately opposite directions.

Taylor determined that there is a minimum condition for the establishment of such vortices, defined as the Taylor number ($T_a$). The Taylor number is dependent upon a number of factors and is defined as $$T_a = \frac{\mu_i d}{\nu} \sqrt{\frac{d}{R_i}} \geq 41.3$$

where d is the gap size, $R_i$ is the radius of the inner rotating cylinder, $\nu$ is the kinematic viscosity of the fluid, and $\mu_i$ is the peripheral velocity of the inner rotating cylinder.

Taylor and other determined that turbulence would ensue if the Reynolds number ($R_a$) rose above about 1000. The Reynolds number is defined as $$R_a = \frac{\omega (zd)}{\nu}$$

where $\omega$ is the axial velocity. More particularly, those skilled in hydrodynamics will appreciate that a time average velocity profile of fluid flow will generate a smooth curve, but an instantaneous velocity profile is very ragged. Thus, the Taylor vortices may be characterized as "main flow", but there will be a turbulent component of this, and as $T_a$ rises, this instantaneous turbulent velocity will ultimately become more important.

Taylor vortices first will develop when the gap is in the range of from 0.010 to 0.020 inches depending on the speed and diameter of the impeller and the viscosity of the fluid. The Taylor number increases with increasing gap dimension. As the gap increases beyond the desired range, the Taylor vortices will be replaced by turbulence which has the unwanted effect of increasing blood damage and increasing prime volume.

In operation, the blood fluid from the patient is directed with a cannula and tubing into flow inlet 12 of housing 10 so that the integrated pump and oxygenator is completely filled with fluid 40. No bubbles or air should be present. The fluid flows onto impeller 30, which is driven by drive shaft 18 causing the incoming fluid to flow radially through flow channels 32. Drive shaft 18 may be driven by any conventional means. For example, a variable speed motor can be connected to the drive shaft. Alternatively, a sealed pump could be used such as that constructed by embedding magnets in the impeller and driven by external magnets. The fluid from flow channels 32 is directed into gap 20 located between the outer edge of the impeller 30 and the innermost portion of mass transfer bed 40 creating a secondary or eddy flow by the tangential flow component coming from the impeller flow channel 32. The net flow from impeller 30 is forced through mass transfer bed 40 where it comes in contact with the fibers 38. An oxygenating fluid is directed into gas inlet header 60 and gas inlet manifold 62 where it then enters lumens 46 of fibers 38. The filters 38, which are made of a gas permeable material, allow oxygen to flow through the fiber membrane wall 44 and into the blood, thus oxygenating it. The remainder of the oxygenating fluid is removed at the gas outlet header 66 and the gas outlet manifold 64. Carbon dioxide may be removed by diffusing through the membrane wall 44 into lumen 46 where is removed through gas outlet header 66 and gas outlet manifold 64 with remaining oxygenating fluid. After the blood is oxygenated, it exits housing 10 at exit manifold 14 where it is then returned to the patient.

The incoming flow rate to the integrated pump and membrane oxygenator of the present invention is determined by the patient's requirements for oxygenation and pumping. Preferably, the flow rates would range from about ½ liter to about 8 liters per minute depending on patient size, with required discharge pressures not greater than about 500 mm Hg.

Utility of the invention is illustrated by the following specific examples.

Figure 5:
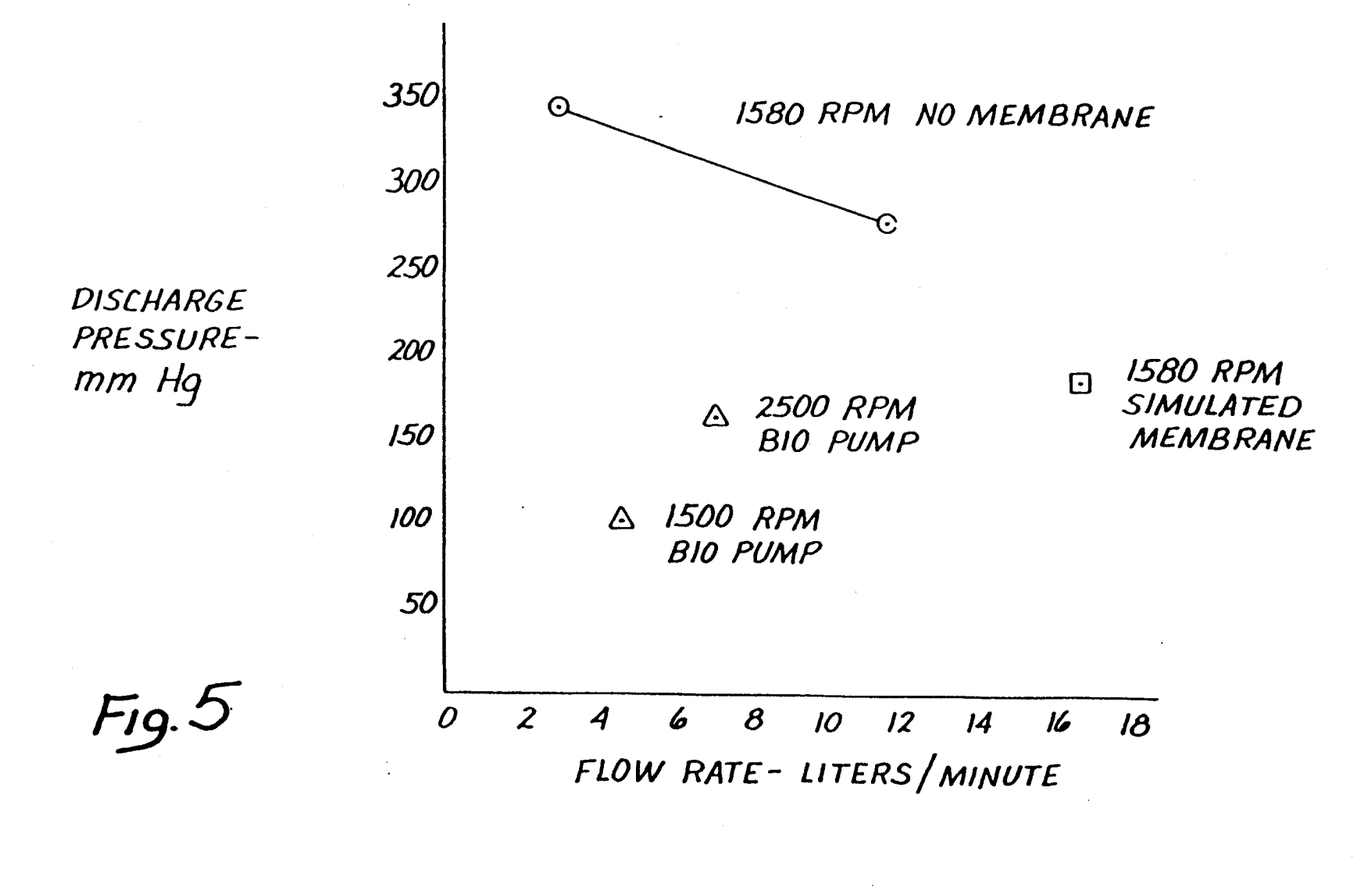
FIG. 5 is a graph depicting the discharge pressure/flow rate performance of the integrated pump and oxygenator of the present invention compared to another known pump.

An engineering model of the integrated pump and membrane oxygenator of the present invention was constructed to test the fluid dynamics. The inside of the housing was 6 inches in diameter and 1½ inches high. The impeller had 4 grooved flow channels and was powered by means of a drillpress motor. The engineering model had a ring constructed of screen material to simulate the fluid mechanics of a membrane bed. The screen material was about 1.5 inches high and 0.75 inches thick and was sealed against the upper and lower housing. Fluid was fed to the housing inlet from a reservoir. The fluid pressure was measured by bordon tube pressure gauge and the flow was measured by timing the delivery of a specific quantity of fluid (water). The results are shown in FIG. 5.

The integrated pump membrane oxygenator of the present invention can be used for partial cardiopulmonary support in emergency situations or for total bypass in the operating room. Where the integrated pump membrane oxygenator is used for partial cardiopulmonary support, it is not necessary to have a reservoir of heat exchanger. A small compliant section, which may be in the form of tubing, between the patient and the pump can be used to monitor the pressure of the fluid to control the speed of the pump motor as necessary. Modest heating and cooling of blood can be accomplished by heating and cooling of the gas supply to the oxygenator. For total support, such as in the operating room, it is preferable to have a reservoir and good heat exchanger. This may be in the form of a combination/modular unit to be put on top of the integrated pump membrane oxygenator when needed.

Since this integration eliminates high pressure connections between pump and oxygenator, the safe use of extracorporeal circulation is greatly improved. Furthermore, the present invention eases the burden of the perfusionist through faster and easier setup, and easier priming and debubbling. And the cost benefit to the manufacturer, over separate pump and oxygenator units, is significant.

While the preferred embodiments of my invention have here been shown and described, it is to be understood that I do not limit myself to the precise construction herein disclosed and that various changes and modifications may be made within the scope of the invention as defined in the appended claims.

I claim:

1. A low priming volume integrated centrifugal pump and membrane oxygenator for pumping and oxygenating blood of a patient during open heart surgery or other emergency situations, said integrated pump and oxygenator comprising:

a housing, said housing containing a first fluid inlet, a first fluid exit, a second fluid inlet and a second fluid exit;

a pump impeller located in said housing, said impeller having flow channels disposed therein and wherein the volume of said flow channels is less than fifty per cent of the total impeller envelope volume available, said impeller further comprising means for rotation;

a mass transfer bed located in said housing and surrounding said impeller, said mass transfer bed comprising a ring of hollow gas permeable membrane fibers running circumferentially around said impeller;

wherein a fluid to be oxygenated is introduced into said housing by means of said first fluid inlet, is pumped radially by said impeller through said channels and into said mass transfer bed and exits said housing by means of said first fluid exit, and an oxygenating fluid is directed through said second fluid inlet into the center of said hollow gas permeable membrane fibers and exits through said second fluid exit.

2. The integrated centrifugal pump and membrane oxygenator of claim 1 wherein said mass transfer bed is formed from a multiple wrap of a fiber ribbon.

3. The integrated centrifugal pump and membrane oxygenator of claim 2 wherein said fiber ribbon comprises at least two layers of fibers bonded together in an alternating arrangement.

4. The integrated centrifugal pump and membrane oxygenator of claim 3 wherein said layers of fibers are bonded together by adhesive point attachment means.

5. The integrated centrifugal pump and membrane oxygenator of claim 3 wherein said layers of fiber are bonded together by adhesive filament means.

6. The integrated centrifugal pump and membrane oxygenator of claim 3 wherein said fiber ribbon layers are spaced in an alternating arrangement so that the fibers in alternate layers are positioned in line with the opening between fibers in the layers above and below.

7. The integrated centrifugal pump and membrane oxygenator of claim 1 wherein said flow channel volume is about 5% to about 50% of the total impeller envelope volume available.

8. The integrated centrifugal pump and membrane oxygenator of claim 1 wherein said flow channel volume is less than about 30% of the total impeller envelope volume available.

9. The integrated centrifugal pump and membrane oxygenator of claim 1 wherein said impeller is comprised of wide vanes and narrow flow channels.

10. The integrated centrifugal pump and membrane oxygenator of claim 1 further comprising an annular region located between said impeller and said mass transfer bed for creating secondary flow therein.

11. The integrated centrifugal pump and membrane oxygenator of claim 10 wherein said annular region comprises a gap located between the outer diameter of said impeller and the inner diameter of said membrane bed.

12. The integral centrifugal pump and membrane oxygenator of claim 11 wherein said gap is between 0.010 inch and 0.100 inch in diameter.

13. A low priming volume integrated centrifugal pump and membrane oxygenator for pumping and oxygenating blood of a patient during open heart surgery or other emergency situations, said integrated pump and oxygenator comprising:

a housing, said housing containing a first fluid inlet, a first fluid exit, a second fluid inlet and a second fluid exit;

an impeller located in said housing having flow channels disposed therein and wherein the volume of said flow channels is less than fifty per cent of the total impeller envelope volume available, said impeller further comprising means for rotation;

a mass transfer bed located in said housing and surrounding said impeller, said mass transfer bed comprising a ring of hollow gas permeable membrane fibers running circumferentially around said impeller;

an annular region located between said impeller and said mass transfer bed;

wherein a fluid to be oxygenated is introduced into said housing by means of said first fluid inlet, is pumped radially by said impeller through said flow channels and into said annular region for creating secondary fluid flow and into said mass transfer bed, and the fluid exits said housing by means of said first fluid exit. and wherein an oxygenating fluid is directed through said second fluid inlet into the center of said hollow gas permeable membrane fibers and exits through said second fluid exit.

14. The integrated centrifugal pump and membrane oxygenator of claim 13 wherein said mass transfer bed is formed from a multiple wrap of fiber ribbon comprising at least two layers of fibers bonded together in an alternating arrangement.

15. The integrated centrifugal pump and membrane oxygenator of claim 14 wherein said fiber ribbon layers are spaced in an alternating arrangement so that the fibers in alternate layers are positioned in line with the opening between fibers in the layers above and below.

16. The integrated centrifugal pump and membrane oxygenator of claim 13 wherein said annular region comprises a gap located between the outer diameter of said impeller and the inner diameter of said membrane bed.

17. The integrated centrifugal pump and membrane oxygenator of claim 13 wherein said flow channels are comprised of vanes having a total volume greater than fifty per cent of the total impeller envelope volume.

18. A low priming volume integrated centrifugal pump and membrane oxygenator for pumping and oxygenating blood of a patient during open heart surgery or other emergency situations, said integrated pump and oxygenator comprising:

a housing, said housing containing a first fluid inlet, a first fluid exit, a second fluid inlet and a second fluid exit;

a pump impeller having flow channels disposed therein and located in said housing, said impeller further comprising means for rotation;

a mass transfer bed located in said housing and surrounding said impeller, said mass transfer bed comprising a ring of hollow gas permeable membrane fibers, each of said fibers running circumferentially around said impeller;

wherein a fluid to be oxygenated is introduced into said housing by means of said first fluid inlet, is pumped radially by said impeller through said channels and into said mass transfer bed and exits said housing by means of said first fluid exit, and an oxygenating fluid is directed through said second fluid inlet into the center of said hollow gas permeable membrane fibers and exits through said second fluid exit.

19. The integrated centrifugal pump and membrane oxygenator of claim 18 wherein said mass transfer bed is formed from a multiple wrap of a fiber ribbon.

20. The integrated centrifugal pump and membrane oxygenator of claim 19 wherein said fiber ribbon comprises at least two layers of fibers bonded together in an alternating arrangement.

21. The integrated centrifugal pump and membrane oxygenator of claim 20 wherein said layers of fibers are bonded together by adhesive point attachment means.

22. The integrated centrifugal pump and membrane oxygenator of claim 20 wherein said layers of fiber are bonded together by adhesive filament means.

23. The integrated centrifugal pump and membrane oxygenator of claim 20 wherein said fiber ribbon layers are spaced in an alternating arrangement so that the fibers in alternate layers are positioned in line with the opening between fibers in the layers above and below.

24. The integrated centrifugal pump and membrane oxygenator of claim 18 wherein said impeller has a flow channel volume that is less than fifty per cent of the total impeller envelope volume available.

25. The integrated centrifugal pump and membrane oxygenator of claim 24 wherein said flow channel volume is about 5% to about 50% of the total impeller envelope volume available.

26. The integrated centrifugal pump and membrane oxygenator of claim 24 wherein said flow channel volume is less than about 30% of the total impeller envelope volume available.

27. The integrated centrifugal pump and membrane oxygenator of claim 24 wherein said flow channels are comprised of vanes having a total volume greater than fifty per cent of the total impeller envelope volume.

28. The integrated centrifugal pump and membrane oxygenator of claim 18 further comprising an annular region located between said impeller and said mass transfer bed for creating secondary flow therein.

29. The integrated centrifugal pump and membrane oxygenator of claim 28 wherein said annular region comprises a gap located between the outer diameter of said impeller and the inner diameter of said membrane bed.

30. The integrated centrifugal pump and membrane oxygenator of claim 29 wherein said gap is between 0.010 inch and 0.100 inch in diameter.

31. A low priming volume integrated centrifugal pump and membrane oxygenator for pumping and oxygenating blood of a patient during open heart surgery or other emergency situations, said integrated pump and oxygenator comprising:

a housing, said housing containing a first fluid inlet, a first fluid exit, a second fluid inlet and a second fluid exit;

an impeller located in said housing having flow channels disposed therein and wherein the volume of said flow channels is less than fifty per cent of the total impeller envelope volume available, said impeller further comprising means for rotation;

a mass transfer bed located in said housing and surrounding said impeller, said mass transfer bed comprising a ring of hollow gas permeable membrane fibers, each of said fibers running circumferentially around said impeller;

an annular region located between said impeller and said mass transfer bed;

wherein a fluid to be oxygenated is introduced into said housing by means of said first fluid inlet, is pumped radially by said impeller through said flow channels and into said annular region for creating secondary fluid flow and into said mass transfer bed, and the fluid exits said housing by means of said first fluid exit, and wherein an oxygenating fluid is directed through said second fluid inlet into the center of said hollow gas permeable membrane fibers and exits through said second fluid exit.

32. The integrated centrifugal pump and membrane oxygenator of claim 31 wherein said mass transfer bed is formed from a multiple wrap of fiber ribbon comprising at least two layers of fibers bonded together in an alternating arrangement.

33. The integrated centrifugal pump and membrane oxygenator of claim 32 wherein said fiber ribbon layers are spaced in an alternating arrangement so that the fibers in alternate layers are positioned in line with the opening between fibers in the layers above and below.

34. The integrated centrifugal pump and membrane oxygenator of claim 31 wherein said annular regions comprises a gap located between the outer diameter of said impeller and the inner diameter of said membrane bed.

35. The integrated centrifugal pump and membrane oxygenator of claim 31 wherein said flow channels are comprised of vanes having a total volume greater than fifty per cent of the total impeller envelope volume.

* * * * *